United States Patent [19]

Davey

[11] Patent Number: 5,026,712
[45] Date of Patent: Jun. 25, 1991

[54] NOVEL IMIDAZO(1,5-A)PYRIDINES, USEFUL AS CARDIOVASCULAR AND CNS AGENTS

[75] Inventor: David D. Davey, Succasunna, N.J.

[73] Assignee: Schering AG, Berlin, Fed. Rep. of Germany

[21] Appl. No.: 507,824

[22] Filed: Apr. 12, 1990

Related U.S. Application Data

[63] Continuation of Ser. No. 741,428, Jun. 5, 1985, abandoned.

[51] Int. Cl.$^5$ .................... A61K 31/41; C07D 471/04
[52] U.S. Cl. .................................. 514/300; 546/121; 546/278; 546/334; 546/329; 546/337
[58] Field of Search ........................ 546/121; 514/300

[56] References Cited

U.S. PATENT DOCUMENTS 4,588,732 5/1986 Browne ............................... 546/121

Primary Examiner—Johann Richter
Attorney, Agent, or Firm—Elizabeth A. Bellamy; John L. White; I. William Millen

[57] ABSTRACT

This invention relates to novel substituted imidazo-[1,5-a]pyridines, most especially novel 8-phenylimidazo-[1,5-a]pyridines. It also relates to novel intermediates and to a novel process for the preparation of certain of these compounds. The compounds of the invention have been found to have significant cardiotonic, antiarrhythmic, hypotensive, CNS stimulant, and other pharmacological effects.

16 Claims, No Drawings ics, and 2-hydroxyethanesulfonic acid, toluenesulfonic, benzenesulfonic, camphorsulfonic, ethanesulfonic acid. The base addition salts may be formed, especially when in Formula I $R_1$ is hydroxy, with the metal ions sodium, potassium, or calcium. The quaternary salts contemplated are those formed when the compounds are reacted with, for example, lower alkyl halides, wherein the halide is selected from iodide, bromide or chloride.

NOVEL IMIDAZO(1,5-A)PYRIDINES, USEFUL AS CARDIOVASCULAR AND CNS AGENTS

CROSS REFERENCE TO RELATED APPLICATIONS

This Application is a continuation of application Ser. No. 06/741,428 filed June 5, 1985, now abandoned.

FIELD OF THE INVENTION

This invention relates to novel imidaze[1,5-a]-pyridines. More especially this invention relates to novel, variously substituted 8-phenylimidazo[1,5-a]-pyridines and their pharmaceutically acceptable acid addition, base addition and quaternary salts. Further encompassed by the invention are novel intermediates produced and utilized therein and a novel process for the production of the imidazo[1,5-a]pyridines. The compounds of the invention exhibit a variety of pharmacological activities for which some pharmaceutical compositions are proposed.

GENERAL DESCRIPTION OF THE INVENTION

COMPOSITION-OF-MATTER ASPECT

In its composition-of-matter aspect, this invention relates to novel imidazo[1,5-a]pyridines. Particularly, this invention relates to novel, variously substituted 8-phenylimidazo [1,5-a]pyridines and their pharmaceutically acceptable acid addition, base addition and quaternary salts of the following Formula I:

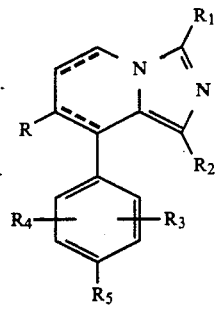

wherein R is hydrogen or lower alkyl;

$R_1$ is hydrogen, lower alkyl, halogen, amino, hydroxy, or trifluoromethyl;

$R_2$ is hydrogen, halogen, lower alkyl, lower alkoxycarbonyl, aminocarbonyl, lower alkylaminocarbonyl or di-lower alkylaminocarbonyl;

$R_3$ and $R_4$ are the same or independently hydrogen, halogen, hydroxy, amino, nitro, lower alkyl, aminocarbonyl, lower alkoxy, lower alkanoylamino or lower alkylsulfonylamino;

$R_5$ is hydrogen, halogen, hydroxy, amino, lower alkyl, lower alkoxy, carboxy, lower alkanoylamino, lower alkylsulfonylamino, or 1-imidazolyl optionally substituted by one or more lower alkyl groups;

and wherein the—lines shall mean the imidazo[1,5-a]-pyridine is in the 5,6,7,8-tetrahydro, 5,6-dihydro, or fully aromatic form.

As used herein the term "halogen" shall mean fluorine, chlorine or bromine. The term "lower" when used in conjunction with the terms alkyl, alkoxy or alkan- shall represent a straight or branched chain alkyl of one to four carbon atoms as for example, methyl, ethyl, propyl, isopropyl, butyl, sec-butyl, isobutyl, and tertiary butyl. When "$R_1$" is defined as hydroxy, the compound shall be taken to be inclusive of its tautomeric keto form.

Also contemplated as part of this invention are the pharmaceutically acceptable acid addition, base addition and quaternary salts of the compounds of Formula I. The acid addition salts may be formed with inorganic or organic acids. Illustrative but not restrictive examples of such acids include hydrochloric, hydrobromic, sulfuric, phosphoric, citric, methanesulfonic, and 2-hydroxyethanesulfonic acid, toluenesulfonic, benzenesulfonic, camphorsulfonic, ethanesulfonic acid. The base addition salts may be formed, especially when in Formula I $R_1$ is hydroxy, with the metal ions sodium, potassium, or calcium. The quaternary salts contemplated are those formed when the compounds are reacted with, for example, lower alkyl halides, wherein the halide is selected from iodide, bromide or chloride.

It is to be understood that the definition of the compounds of formula I encompasses all possible stereoisomers and mixtures thereof, which possess the activities discussed below. In particular, it encompasses the geometrical and optical isomers and the racemic modifications thereof which possess the indicated activity.

The most preferred compounds of this invention are those of the above general Formula I having the characteristics wherein $R_3$ and $R_4$ are hydrogen and $R_5$ is hydroxy, lower alkylsulfonylamino, or 1-imidazolyl optionally substituted by 1 or more lower alkyl groups.

The compounds which follow are some of those which serve to exemplify the various composition-of-matter and/or process aspects concerned with the compounds of general Formula I as described herein.

(1) 8-(4-Chlorophenyl)-5,6-dihydro-3-methylimidazo-[1,5-a]pyridine.

(2) 5,6-Dihydro-8-(4-hydroxyphenyl)-3-methylimidazo-[1,5-a]pyridine.

(3) 5,6-Dihydro-8-(4-ethoxyphenyl)-3-methylimidazo-[1,5-a]pyridine.

(4) 8-[4-(Acetylamino)phenyl]-5,6-dihydro-3-methylimidazo[1,5-a]pyridine.

(5) 5,6-Dihydro-3-methyl-8-[4-((methylsulfonyl)amino)-phenyl]imidazo[1,5-a]pyridine.

(6) 8-(4-Ethoxyphenyl)-3-methylimidazo[1,5-a]pyridine.

(7) 5,6-Dihydro-3-methyl-8-(4-methylphenyl)imidazo-[1,5-a]pyridine.

(8) 2,3-Dihydro-8-(4-methylphenyl)-3-oxoimidazo[1,5-a]-pyridine-1-carboxylic acid methyl ester.

(9) 8-(3,4-Dichlorophenyl)-5,6-dihydro-3-methylimidazo-[1,5-a]pyridine.

(10) 8-(4-Methylphenyl)imidazo[1,5-a]pyridin-3(2H)-one.

(11) 8-(4-Chlorophenyl)-5,6-dihydro-3-ethyl-1-methyl-imidazo[1,5-a]pyridine.

(12) 3-Methyl-8-(4-methylphenyl)imidazo[1,5-a)pyridine.

(13) 5,6-Dihydro-3-methyl-8-phenylimidazo[1,5-a]pyridine.

(14) 3-MethYl-8-phenylimidazo[1,5-a]pyridine.

(15) 2,3-Dihydro-3-oxo-8-phenylimidazo[1,5-a]pyridine-1-carboxylic acid ethyl ester.

(16) 3-Methyl-8-[4-((methylsulfonyl)amino)phenyl]-5,6,7,8-tetrahydroimidazo[1,5-a]pyridine.

(17) 2,3-Dimethyl-8-[4-((methylsulfonyl)amino)-phenyl]-5,6,7,8-tetrahydroimidazo[1,5-a]pyridinium iodide.

(18) 5,6-Dihydro-2,3-dimethyl-8-[4-((methylsulfonyl)-amino)phenyl]imidazo[1,5-a]pyridinium iodide.

(19) 5,6-Dihydro-3-methyl-8-[4-(2-methyl-1H-imidazol-1-yl)phenyl]imidazo[1,5-a] pyridine.

(20) 5,6-Dihydro-3-ethyl-8-[(4-(2-ethyl-1H-imidazol-1-yl)-phenyl]imidazo[1,5-a]pyridine.

(21) 5,6-Dihydro-8-[4-(1H-imidazol-1-yl)phenyl]-3-methyl-imidazo[1,5-a]pyridine.

(22) 3-Methyl-8-[4-(2-methyl-1H-imidazol-1-yl)phenyl]-imidazo[1,5-a]pyridine.

(23) 1-Bromo-3-methyl-8-[4-(2-methyl-1H-imidazol-1-yl)-phenyl]imidazo[1,5-a]pyridine.

(24) 4-(Imidazo[1,5-a]pyridin-8-yl)benzoic acid.

(25) 3,7-Dimethyl-8-[4-(1H-imidazol-1-yl)phenyl]imidazo-[1,5-a]pyridine.

(26) 2,3-Dihydro-8-[4-(1H-imidazol-1-yl)phenyl]-7-methyl-3-oxoimidazo[1,5-a] pyridine-1-carboxylic acid ethyl ester.

(27) 8-[4-Chlorophenyl)imidazo[1,5-a]pyridin-3-amine.

(28) 3-Ethyl-1-methyl-8-(4-nitrophenyl)imidazo[1,5-a]-pyridine.

A further aspect of this invention relates to certain novel intermediates, which intermediates are derived from certain of the compounds of general Formula I which are then further reacted to obtain still other novel compounds general Formula I. The novel intermediates considered as part of this invention are those illustrated by the following Formula II:

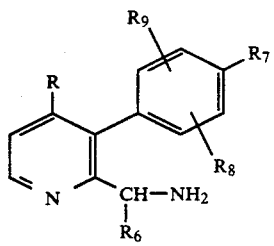

II wherein R and $R_6$ are hydrogen or lower alkyl;

$R_7$ is hydrogen, hydroxy, chlorine, nitro, amino, lower alkyl, lower alkoxy, lower alkanoylamino, lower alkylsulfonylamino or 1-imidazolyl optionally substituted by 1 or more lower alkyl groups;

$R_8$, $R_9$ are the same or independently hydrogen, halogen, hydroxy, amino, lower alkyl, lower alkoxy, or lower alkylsulfonylamino.

Representative of some of the compounds of this invention which are intermediary in nature and defined by the above general Formula II are the following:

(a) 2-(Aminomethyl)-3-(4-methylphenyl)pyridine,
(b) 2-(Aminomethyl)-3-[4-(2-methyl-1H-imidazol-1-yl)-phenyl]pyridine,
(c) 2-(Aminomethyl)-3-phenylpyridine,
(d) 2-(Aminomethyl)-3-(4-chlorophenyl)pyridine,
(e) 2-(1-Aminoethyl)-3-(4-chlorophenyl)pyridine,
(f) 2-(Aminomethyl)-3-[(1H-imidazol-1-yl)phenyl]-4-methylpyridine.

PROCESS ASPECTS

Certain of the compounds of this invention may be prepared by standard techniques analogous to those known in the art. However, this invention also provides a new and novel method for the synthesis of imidazo[1,5-a]-pyridine derivatives. This novel synthesis offers the advantage of obtaining the 8-phenylimidazo[1,5-a]pyridines of this invention from readily available starting materials.

In general, the novel process involves the reaction of a 2-alkylimidazole with a phenyl cyclopropyl ketone or a 4-halobutyrophenone to produce in one step a variety of 8-phenyl-5,6-dihydro-3-alkylimidazo[1,5-a]pyridines. These compounds, novel in themselves, may be further reacted t produce still other compounds of the invention. For example, they may be ring opened to produce the novel intermediate 2-alkylamino-3-phenylpyridines of this invention, which intermediates may be reacted to produce still other 8-phenylimidazo[1,5-a]pyridines.

A schematic of the process follows:

Scheme A

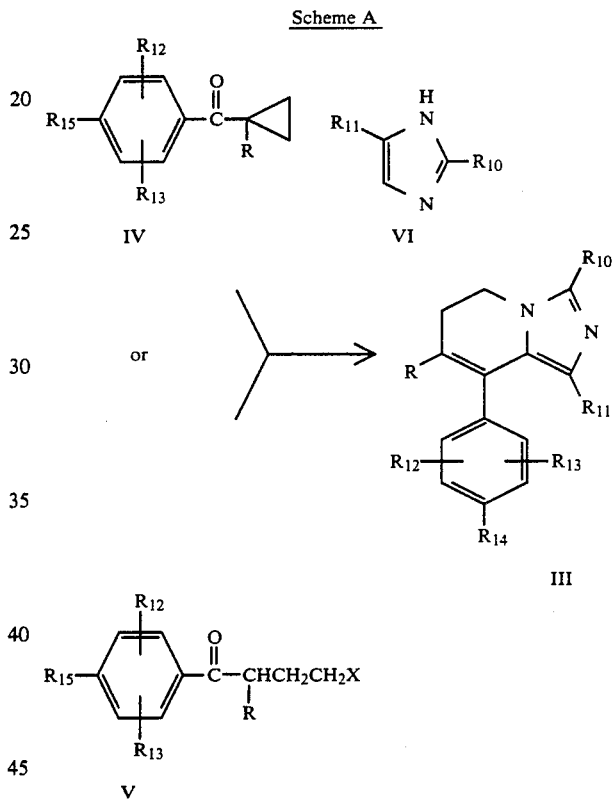

In the foregoing Scheme A, X is chlorine or bromine, R is as previously defined; $R_{10}$ is lower alkyl; $R_{11}$ is hydrogen or lower alkyl; $R_{12}$, $R_{13}$ are the same or independently hydrogen, halogen, hydroxy, lower alkyl, lower alkoxy, lower alkanoylamino or lower alkylsulfonylamino; $R_{14}$ is hydrogen, chlorine, bromine, hydroxy, lower alkoxy, lower alkyl, lower alkanoylamino, lower alkylsulfonylamino or 1-imidazolyl optionally substituted by 1 or more lower alkyl groups; $R_{15}$ is hydrogen, halogen, hydroxy, lower alkyl, lower alkoxy, lower alkanoylamino, lower alkylsulfonylamino, or 1-imidazolyl optionally substituted by 1 or more lower alkyl groups.

The process of Scheme A is carried out by heating 1 equivalent of a compound of Formulae IV or V neat with 3-10 equivalents of a compound of Formula VI in a temperature range of from about 100° C. to about 250° C., preferably in the range of about 175° C. to about 225° C. for about 12 to about 48 hours. Alternatively, the reactants instead of being heated in a neat state, can be heated in the presence of 1 equivalent of an inorganic acid such as hydrochloric or hydrobromic acids. The product may then be isolated by crystallization or column chromatography.

The foregoing method represents a novel synthesis for the preparation of imidazo[1,5-a]pyridine derivatives from the preformed imidazole. Standard methods start with the acetylation of 2-aminomethylpyridines followed by ring closure with phosphorus oxychloride. However, this method would require 3-phenyl-2-aminomethylpyridines as starting materials to obtain the compounds of this invention; such compounds appear to be unavailable in the literature. The instant method offers the advantage of being able to prepare 8-phenyl derivatives from readily available starting materials, that is, available through the chemical catalogs or easily fabricated by methods known in the art.

The meanings for $R_{14}$ and $R_{15}$ differ in the foregoing scheme in the fact that if $R_{15}$ is fluorine, the imidazole will displace it thus providing compounds of the invention, i.e. Formula III wherein $R_{14}$ is 1-imidazolyl.

The compounds of Formula III can be further transformed to produce still other compounds of the general Formula I.

The following Scheme B is illustrative of such transformations.

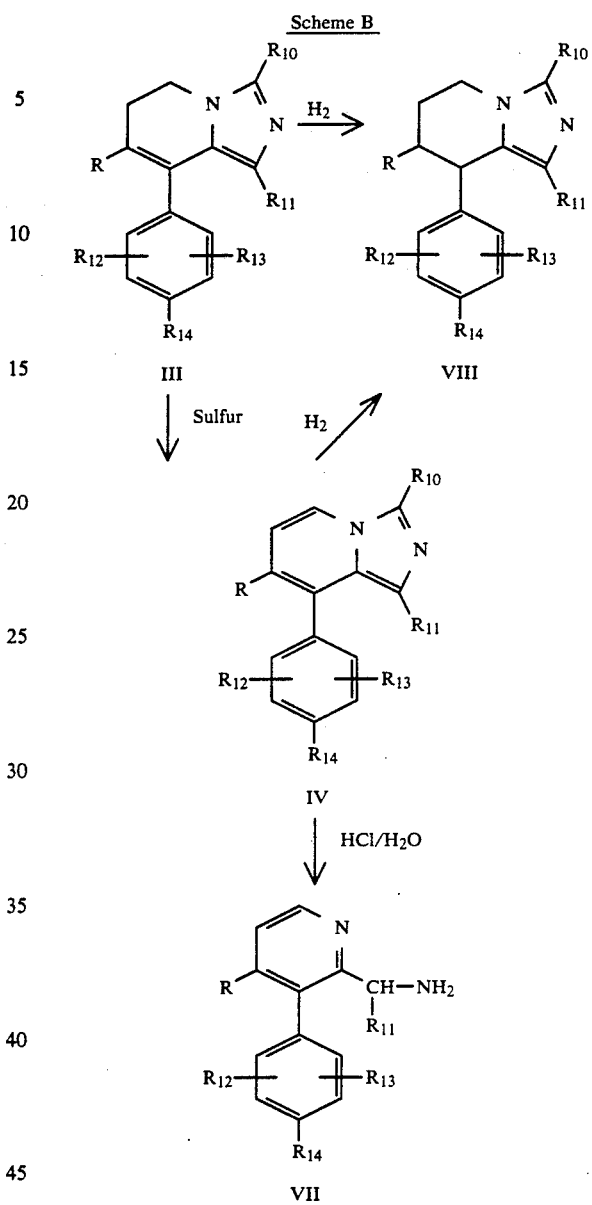

In the foregoing Scheme B the 5,6-dihydro compound of Formula III may be hydrogenated in the presence of catalysts such as palladium on carbon to give the tetrahydro derivatives of Formula VIII.

Compounds of Formula III may also be dehydrogenated to form the fully aromatic derivatives of Formula VI. This dehydrogenation can be accomplished in several ways, as for instance, with sulfur in a suitable solvent such as decalin at about 100–200° C.; or with manganese dioxide in a suitable solvent such as methylene chloride at a temperature of about 0–45° C.

The aromatic compounds of Formula VI may be hydrolyzed in aqueous acid such as hydrochloric acid at a temperature of about 60° C. to about 110° C. to give the novel 3-phenyl-2-aminomethylpyridines of Formula VII. These compounds are valuable and novel intermediates which when further derivatized to other 3-phenyl-2-aminomethylpyridines constitute the novel compounds of the general Formula II. The compounds of Formula VII or further derivatives thereof may be reacted to form still other compounds of the general Formula I.

The conversion of the compounds of Formula VII to other novel compounds of Formula I is illustrated in the following Scheme C.

Formula VII, $R_{11}$ is hydrogen, then Formula XII is formed which may be further treated with TMSI or by hydrogenation over Pd. The choice of the reactants will be dependent on $R_{17}$, whether lower alkyl or arylalkyl.

METHOD-OF-USE AND PHARMACEUTICAL COMPOSITION ASPECT

Scheme C

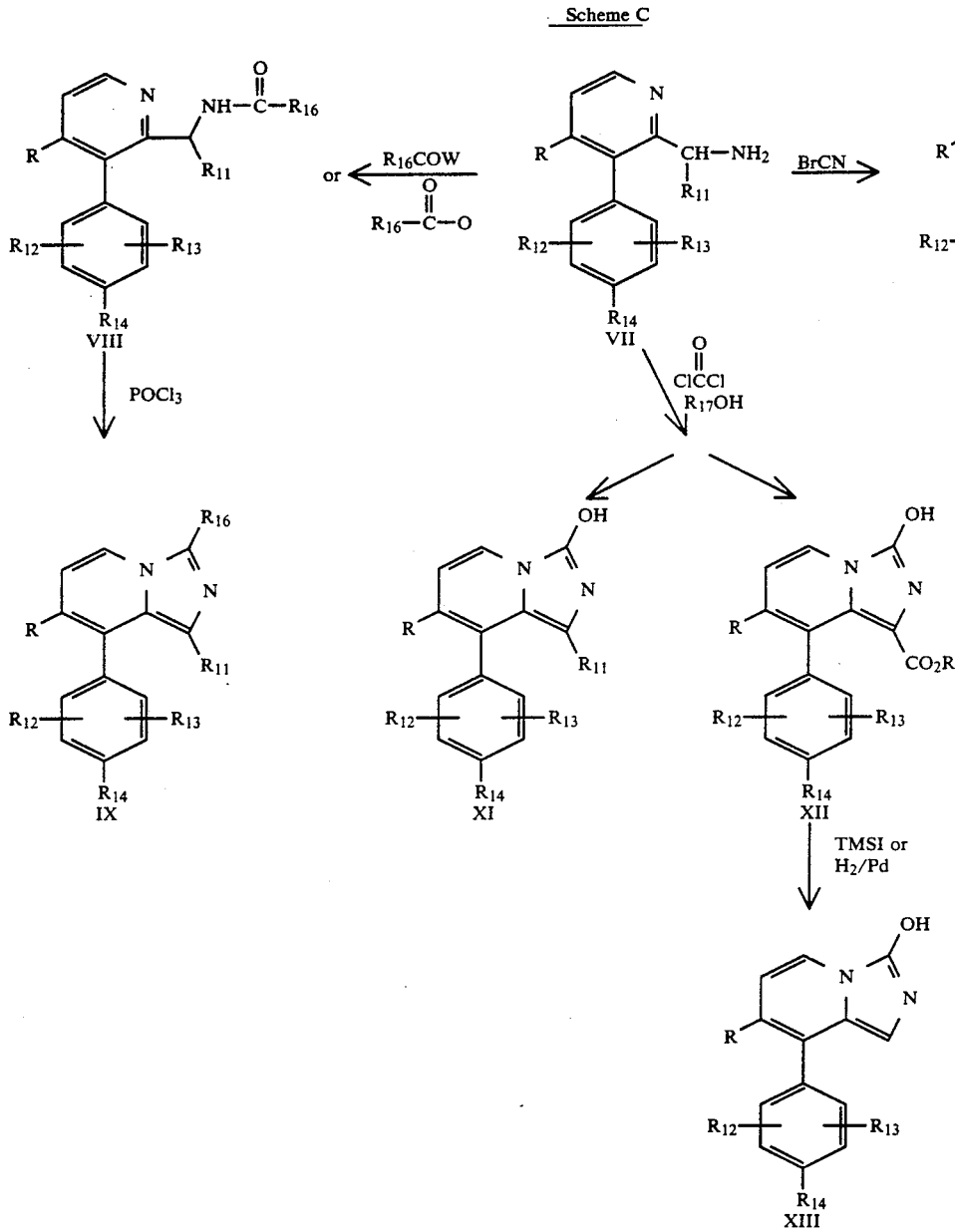

In the foregoing Scheme C, W is chlorine or hydroxy; $R_{16}$ is hydrogen, lower alkyl or trifluoromethyl; $R_{17}$ is lower alkyl or arylalkyl; R, $R_{11}$, $R_{12}$, $R_{13}$, $R_{14}$ have the same meanings as above. As is illustrated above, compounds of Formula VII may be acetylated to produce compounds of Formula VIII which can be then ring closed to Formula IX with the use of phosphorus oxychloride. In another reaction compounds of Formula VIII can be converted to compounds of Formula X with the use of cyanogen bromide. Still another procedure involves reaction of Formula VII with phosgene and an alcohol. In the mixture when $R_{11}$ in Formula VII is alkyl, then Formula XI is formed. When in The novel 8-phenylimidazo[1,5-a]pyridines of this invention and their pharmaceutically acceptable acid addition, basic addition and quaternary salts have been found to possess a number of important pharmacological characteristics when applied in a number of forms to mammals. Compounds of the general Formula I have been found to possess significant cardiotonic, antiarrhythmic, hypotensive and CN stimulant effects.

The compounds were tested for their cardiotonoic activity in the isolated cat papillary muscle screen [J. Wiggins, Circ. Res. 49, 718–725 (1981)] and their action was attributed to their ability to increase contractile force in cardiac muscle with minimal effects on heart rate or blood pressure. The compounds were found to have either a short or long term duration of activity. Those of short term would be useful in the treatment of acute heart failure whilst those of long term activity would be useful not only for this indication but useful for the treatment of chronic or congestive heart failure. Illustrative, but not exclusive, of the compounds exhibiting significant cardiotonic activity are the following: 5,6-dihydro-8-(4-hydroxyphenyl)-3-methylimidazo [1,5-a]pyridine; 5,6-dihydro-3-methyl-8-[4-(2-methyl-1H-imidazol-l-yl)phenyl] imidazo[1,5-a]pydidine; 5,6-dihydro-3-methyl-8-[4-((methylsulfonyl)amino)phenyl]imidazo [1,5-a]pyridine; 5,6-dihydro-8-[4-(1H-imidazol-1yl)phenyl]-3-methylimidazo[1,5-a] pyridine; 3-methyl-8-[4((methylsulfonyl)amino)phenyl]-5,6,7,8-tetrahydroimidazo [1,5-a]pyridine.

The antiarrhythmic activity of the compounds was measured by their ability to prolong the action potential of cardiac tissue. Those compounds demonstrating this prolongation of effect are designated in the Vaughan Williams classification as Class III agents and thus are valuable in the treatment of cardiac arrhythmias especially those of the re-entrant type and particularly those associated with the disease state known as chronic ventricular tachycardia. Illustrative of such types of compounds is 5,6-dihydro-2,3-dimethyl-8-[4-((methyl-sulfonyl)amino)phenyl] imidazo[1,5-a]pyridinium iodide.

Blood pressure lowering effects, indicative of vasoactive activity, were measured in the standard autonomic screen utilizing the SH-rat. Compounds of the type as 2,3-dihydro-8-(4-methylphenyl)-3-oxoimidazo-[1,5-a] pyridine-1-carboxylic acid methyl ester; 8-(4methylphenyl)imidazo-[1,5-a]pyridin-3(2H)-one; 2,3-dihydro-3-oxo-8-phenylimidazo[1,5-a]pyridine-1-carboxylic acid ethyl ester; have been found to relax venous tissue in vitro suggesting their potential use in improving coronary perfusion in the failing heart.

CNS tests were conducted using standard neuropharmacological screens such as measuring barbiturate sleeping time, motor activity, gait, etc. to determine the CNS profile. Compounds such as 5,6-dihydrO-3-ethyl-8-[(4-(2-ethyl-1H-imidazol-l-yl)phenyl] imidazo[1,5-a]-pyridine and 3-methyl-8-[4-(2-methyl-1H-imidazol-1-yl)phenyl] imidazo[1,5-a]pyridine have been found to be particularly effective in counteracting barbiturate anesthesia and centrally related respiratory depression.

In some cases multiple effects are manifest in a particular compound, while in other cases one or another of these effects is found in a particular compound. The compounds can be administered orally or parenterally. The dosage and method of administration will be dependent on the age, weight, sex and other characteristics of the subject to be treated and the disease state to be treated. The compounds when administered orally or parenterally will be admixed with pharmaceutically acceptable carriers in accordance with standard pharmaceutical practices taking into account the compound to be administered, its dosage form and the disease state it is to effect.

The invention described hereinabove is illustrated below in the Preparations and Examples which, however, is not to be construed as limiting the invention.

PREPARATIONS

Preparation 1

2-(Aminomethyl)-3-(4-methylphenyl)pyridine

Add 32 g (0.14 mol) of the product of Example IX to 400 ml of 6N hydrochloric acid and heat to reflux for 20 hr. Neutralize with potassium hydroxide and extract with 2×500 ml of methylene chloride. Combine the extracts, dry over magnesium sulfate, and remove the solvent in vacuo. Kugelrohr distill the residue to provide the title compound.
NMR (CDCl$_3$):δ=175(s,2), 2.41(s,3), 3.92(s,2), 7.20-7.30(m,5, 7.52(d,1), and 8.57(d,1)ppm.

Preparation 2

2-(Aminomethyl)-3-[4-(2-methyl-1H-imidazol-1-yl)phenyl]-pyridine

Add 7 g (24.3 mmol) of the product of Example XIV to 300 ml of 6N hydrochloric acid and heat to reflux for 20 hr. Neutralize with potassium carbonate and extract with 2×400 ml of methylene chloride. Combine the extracts, dry over sodium sulfate, treat with charcoal, and remove the solvent in vacuo. Crystallize the residue from ether to provide the title compound.
NMR (DMSO):δ=2.35(s,3), 2.50(s,2), 3.76(s,2), 6.94(d,1), 7.36(d,1), 7.38(m,1),7.56(d,2), 7.59(d,2), 7.61(d,1), and 8.60(d,1)ppm.

Preparation 3

2-(Aminomethyl)-3-phenylpyridine

Add 160 g (0.77 mol) of the product from Example XIX to 1.3 liters of 6N hydrochloric acid, and heat to reflux for 24 hr. Cool to room temperature and wash with 2× 1 liter of methylene chloride. Neutralize with potassium hydroxide and extract with 2×1 liter of ether. Combine the extracts, dry over magnesium sulfate, and remove the solvent in vacuo. Kugelrohr distill the residue at 100-110° C. at 0.5 mm Hg to provide the title compound. NMR (CDCl$_3$): δ=1.78(s,2), 3.92(s,2), 7.23-7.54(m,7) and 8.60(d,1 )ppm.

EXAMPLES

Example I 8-(4-(Chlorophenyl)-5,6-dihydro-3-methylimidazo[1,5-a]-pyridine 25 g (0.14 mol) of 4-chlorophenyl cyclopropyl ketone is combined with 50 g (0.61 mol) of 2-methylimidazole and heated to 200° C. under nitrogen for 24 hr. Isolation from 200 g of silica gel (methylene chloride as solvent) provides the title compound.
NMR (CDCl$_3$):δ=2.40(s,3), 2.50-2.90(m,2), 3.80-4.20(t,2), 5.70-5.90(t,1), 6.90(s,1), and 7.30-7.70(m,4)ppm.

Example II 5,6-Dihydro-8-(4-hydroxypheny)-3-methylimidazo[1,5-a]-pyridine 25 g (0.14 mol) of cyclopropyl 4-methoxyphenyl ketone is combined with 50 g (0.61 mol) of 2-methylimidazole and heated to 225° C. under nitrogen for 16 hr. The reaction is extracted with sodium hydroxide solution and the extract neutralized with ammonium chloride. Recrystallization from methylene chloride/methanol (1:1) provides the title compound.

NMR (CF$_3$COOH): δ=2.70–3.20(m,5), 4.10–4.50(t,2), 6.30–6.50(t,1), and 7.00–7.50(m,5)ppm.

Example III 5,6-Dihydro-3-methyl-8-[4-(2-methyl-1H-imidazol-1-yl)-phenyl]imidazo[1,5-a]pyridine 50 g (0.25 mol) of 4-chloro-4'-fluorobutyrophenone are combined with 130 g (1.58 mol) of 2-methylimidazole and heated to 200° C. under nitrogen for 18 hr. Crystallization from ethyl acetate provides the title compound.

NMR (CDCl$_3$):δ=2.50(d,6), 2.60–3.00(M,2), 3.80–4.20(t,2), 5.80–6.00(t,1),6.90(s,1), 7.20(s,2), and 7.30–8.00(m,4)ppm.

Example IV 5,6-Dihydro-8-(4-ethoxyphenyl)-3-methylimidazo[1,5-a]-pyridine

Combine 150 g (0.66 mol) of 4-chloro-4'-ethoxybutyrophenone with 300 g (3.65 mol) of 2-methylimidazole and heat to 175° C. for 18 hr. Crystallization from ethyl acetate provides the title compound.

NMR (CDCl$_3$): δ=1.43(t,3), 2.41(s,3), 2.61(quar,2), 3.92(t,2), 4.05(quar,2), 5.77(t,1),6,84(s,1), 6.99(d,2), and 7.41(d,2)ppm.

Example V

8-[4-(Acetylamino)phenyl]-5,6-dihydro-3-methylimidazo[1,5-a]pyridine

Combine 20 g (83.4 mmol) of N-[4-(4-chloro-1-oxobutan-1-yl)phenyl] acetamide with 50 g (0.61 mol) of 2methylimidazole and heat to 175° C. for 18 hr. Crystallization from ethyl acetate provides the title compound.

NMR (DMSO):δ=2.05(s,3), 2.30(s,3), 2.57(m,2), 3.93(t,2), 5.83(t,1), 6.68(s,1), 7.40(d,2), 7.61(d,2), and 10.01(s1)ppm.

Example VI 5,6-Dihydro-3-methyl-8-[4-((methylsulfonyl)amino)-phenyl]-imidazo[1,5-a]pyridine Combine 100 g (0.36 mol) of N-[(4-chloro-1-oxobutyl)phenyl] methanesulfonamide with 400 g (4.88 mol) of 2-methylimidazole and heat to 175° C. for 22 hr under argon. Crystallization from methylene chloride provides the title compound.

NMR (DMSO):δ=2.32(s,3), 2.57(quar,2), 3.02(s,3), 3.94(t,2), 5.84(t,1), 6.70(s,1), 7.24(d,2), 7.44(d,2), and 9.90(s,1) ppm.

Example VII 8-(4-Ethoxyphenyl)-3-methylimidazo[1,5-a]pyridine

Combine 15 g (59 mmol) of the product of Example IV with 150 g of manganese dioxide in 500 ml of methylene chloride and heat at reflux for 24 hr. Filter off the solids and remove the solvents under vacuum. Crystallize the residue from ethyl acetate to provide the title compound.

NMR (DMSO):δ=1.30(t,3), 2.60(s,3), 4.10(quar,2), 6.70(m,2), 7.10(d,2), 7.70(d,2), and 8.10(d,1)ppm.

Example VIII 5,6-Dihydro-3-methyl-8-(4-methylphenyl)imidazo[1,5-a]-pyridine

Combine 50 g (0.25 mol) of 4-chloro-4'-methylbutyrophenone with 124 g (1.5 mol) of 2-methylimidazole and heat to 175° C. for 70 hr. Crystallize from ether to provide the title compound.

NMR (CDCl$_3$):δ=2.38(s,3), 2.41(s,3), 2.63(quar,2), 3.92(t,2), 5.77(t,1), 6.84(s,1), 7.19(d,2), and 7.38(d,2)ppm.

Example IX

3-Methyl-8-(4-methylphenyl)imidazo[1,5-a]pyridine

Combine 20 g (89.2 mmol) of the product of Example VIII with 5 g (0.16 mol) of sulfur in 250 ml of decalin and heat to 180–190° C. under nitrogen for 7 hr. Extract the reaction with 2 liters of 2N sulfuric acid solution. Charcoal treat the extract and neutralize with potassium carbonate. Extract the aqueous portion with 800 ml of ethyl acetate, dry over magnesium sulfate, treat with charcoal, and remove the solvents under vacuum. Crystallize from ether to provide the title compound.

NMR (CDCl$_3$):δ=2.38(s,3), 2.62(s,3), 6.75–6.78(m,2), 7.33–7.34(m,3), 7.61(d,2), and 8.07(d,1)ppm.

Example X 2,3-Dihydro-8-(4-methylphenyl)-3-oxoimidazo[1,5-a]-pyridine-1-carboxylic acid methyl ester To 100 ml of 12.5% phosgene in benzene at −10° C. add a solution of 5 g (25.2 mmol) of 2-aminomethyl-3-(4-methylphenyl)pyridine (Preparation 1), 3 g (25.2 mmol) of N,N-dimethylaniline, and 50 ml of toluene over a 1 hour period. Allow the reaction to warm to room temperature, then heat to 50° C. for 1 hour. Cool to room temperature and filter off solids. Place the solids in 300 ml of methanol and heat to 50° C. for 1 hr. Remove the solvent in vacuo, dissolve the residue in 200 ml of ethyl acetate and wash with 2×100 ml of 10% hydrochloric acid. Dry over magnesium sulfate, treat with charcoal, and remove the solvent in vacuo. Crystallize from ether to provide the title compound.

NMR (CDCl$_3$):δ=2.42(s,3), 3.31(s,3), 6.54(t,1), 6.83(d,1), 7.21(s,4), 7.94(d,1), and 9.90(s,1)ppm.

Example XI 5,6-Dihydro-3-ethyl-8-[4-(2-ethyl-1H-imidazol-1-yl)phenyl] imidazo[1,5-a]pyridine Combine 155 g of (0.94 mol) of cyclopropyl-(4-fluorophenyl)methanone with 300 g (3.1 mol) of 2-ethylimidazole and heat to 175° C. under argon for 18 hr. The title compound is isolated by column chromatography on 1500 g of silica gel using 2% methanol/methylene chloride as solvent.

NMR (CDCl$_3$):δ=1.29(t,3), 1.37(t,3), 2.50–2.70(m,6), 3.99(t,2), 5.89(t,1), 6.89(s,1), 7.02(d,1), 7.08(d,1), 7.32(d,2), and 7.59(d,2) ppm.

Example XII 5,6-Dihydro-8-[4-(1H-imidazol-1-yl)pheny]-3-methylimidazo-[1,5-a]pyridine Combine 100 g (0.47 mol) of cyclopropyl-[4-(1H-imidazol-1-yl)phenyl]methanone with 300 g (3.7 mol) of 2methylimidazole and heat to 175° C. under argon for 14 hr. Crystallization from acetonitrile provides the title compound.

NMR (CDCl$_3$):δ=2.43(s,3), 2.68(quar,2), 3.97(t,2), 5.86(t,1), 6.85(s,1), 7.24(d,1), 7.31(d,1), 7.41(d,2), 7.61(d,1), and 7.92(s,1)ppm,

Example XIII (3,4-Dichlorophenyl)-5,6-dihydro-3-methylimidazo[1,5-a]pyridine Combine 10 g (46.5 mmol) of cyclopropyl-3,4dichlorophenyl)methanone with 20 g (0.24 mol) of 2-methylimidazole and heat to 175° C. under nitrogen for 70 hr. The title compound is isolated by column chromatography on silica gel using methylene chloride as the solvent.

NMR (CDCl₃):δ=2.42(s,3), 2.66(quar,2), 3.94(t,2), 5.82(t,1), 6.82(S,1), 7.31(d,1), and 7.57(s,1)ppm.

Example XIV

3-Methyl-8-[4-(2-methyl-1H-imidazol-1-yl)phenyl-]imidazo-[1,5-a]pyridine

Combine 24 g (82.7 mmol) of the product of Example III with 10 g (0.31 mol) of sulfur in 500 ml of 1,2-dichlorobenzene and heat to reflux under nitrogen for 13 hr. Cool to room temperature and extract with 2× 500 ml of 10% hydrochloric acid. Combine the extracts and wash with 1 liter of methylene chloride and 500 ml of ethyl acetate. The aqueous phase is treated with charcoal, filtered, neutralized with sodium hydroxide, and extracted with 2×500 ml of methylene choride. Dry the combined extracts over magnesium sulfate and charcoal treat. Concentrate under vacuum to 200 ml rotal volume and isolate the title compound by column chromatography on 300 g of silica gel using 2% methanol/methylene chloride as solvent.

NMR (CDCl₃):δ=2.45(s,3), 2.71(s,3), 6.72(m,2), 7.07(d,1), 7.08(d,1), 7.42(d,2), 7.49(s,1), 7.75(d,1), and 7.81(d,2)ppm.

Example XV

1-Bromo-3-methyl-8-[4-(2-methyl-1H-imidazol-1-yl)phenyl]imidazo[1,5-a]pyridine

Combine 2.2 g (7.6 mmol) of the product of Example XIV with 1.4 g (7.9 mmol) of N-bromosuccinimide in 50 ml of methylene chloride and stir at room temperature for 1 hr. Wash the reaction with 100 ml of 10% potassium carbonate solution, dry over magnesium sulfate, treat with charcoal, and remove the solvent in vacuo. Crystallize the residue from ether to provide the title compound.

NMR (CDCl₃):δ=2.43(s,3), 2.69(s,3), 6.64–6.70(m,2), 7.07(s,1), 7.09(s,1), 7.37(d,2), 7.54(d,2), and 7.72(d,1)ppm.

Example XVI 8-(4-Chlorophenyl)-5,6-dihydro-3-ethyl-1-methylimidazo[1,5-a]pyridine Combine 25 g (0.14 mol) of 4-chlorophenyl cyclopropyl ketone with 50 g (0.45 mol) of 2-ethyl-4-methylimidazole, and heat to 175° C. under argon for 40 hr. Isolate the title compound by column chromatography on 500 g of silica gel using 1% methanol/methylene chloride as solvent.

NMR (CDCl₃):δ=1.32(t,3), 1.77(s,3), 2.55(quar,2), 2.70(quar,2), 3.88(t,2), 5.64(t,1), and 7.25–7.35(m,4)ppm.

Example XVII 8-(4-Methylphenyl)imidazo[1,5-a]pyridin-3(2H)-one

Combine 18 g (64 mmol) of the product of Example X with 19 ml (0.13 mol) of iodotrimethylsilane in 500 ml of methylene chloride and heat to reflux for 24 hr. Cool to room temperature and pour the reaction into 1 liter of 10% potassium carbonate. Dry the methylene chloride portion over magnesium sulfate, treat with charcoal, and remove the solvent in vacuo. Crystallize from ether to provide the title compound.

NMR (CDCl₃):δ=2.42(s,3), 6.25(t,1), 6.45(d,1), 6.60(s,1), 7.25(d,2), 7.47(d,2), 7.57(d,1), and 11.56(s,1)ppm.

Example XVIII 5,6-Dihydro-3-methyl-8-phenylimidazo[1,5-a]pyridine

Combine 270 g (1.48 mol) of 4-chlorobutyrophenone with 600 g (7.3 mol) of 2-methylimidazole and heat to 175° C. for 24 hr. Crystallization from ether provides the title compound.

NMR (CDCl₃):δ=2.41(s,3), 2.65(m,2), 3.94(t,2), 5.80(t,1), 6.84(s,1), and 7.30–7.60(m,5)ppm.

Example XIX

3-Methyl-8-phenylimidazo[1,5-a]pyridine

Add 250 g (1.2 mol) of the product from Example XVIII to a solution of 75 g (2.3 mol) of sulfur in 1.5 liters of decalin and heat to 180–190° C. under nitrogen for 6 hr. Cool to room temperature and extract with 2-1.5 liters of 2N sulfuric acid. Combine the acid extracts and make basic with potassium hydroxide, then wash with 2×1 liter of methylene chloride. Combine the methylene chloride extracts, dry over sodium sulfate, treat with charcoal, and remove the solvent in vacuo. Crystallize the residue from ether to provide the title compound.

NMR (CDCl₃):δ=2.69(s,3), 6.66(m,2), 7.46(m,4), and 7.68(m,3)ppm.

Example XX 2,3-Dihydro-3-oxo-8-phenylimidazo[1,5-a]pyridine-1-carboxylic acid ethyl ester Add a solution of 25 g (0.14 mol) of 2-aminomethyl-3-phenylpyridine (Preparation 3), 34 ml of N,N-dimethylaniline, and 100 ml of toluene to 500 ml of a 12.5% solution of phosgene in toluene at −5° C. over 0.5 hr. Warm slowly to 50–60° C. for 1 hr. Cool to room temperature and pour the reaction mixture into 500 ml of ethanol. Stir for 30 minutes and remove the solvent in vacuo. Crystallize the residue from ether to provide the title compound.

NMR (CDCl₃): δ=0.88(t,3), 3.84(quar,2), 6.59(t,1), 6.83(d,1), 7.30–7.40(m,5), 7.93(d,1), and 9.93(s,1)ppm.

Example XXI

3-Methyl-8-[4-((methylsufonyl)amino)phenyl]-5,6,7,8-tetrahydroimidazo[1,5-a]pyridine Dissolve 5 g (16.5 mmol) of the product from Example VI in 100 ml of 1N sodium hydroxide and hydrogenate over 2 g of 10% palladium on carbon at 50 psi for 16 hr. Remove the catalyst and neutralize the filtrate with ammonium chloride. Extract wih 2×100 ml of methylene chloride. Dry the combined extracts over sodium sulfate and remove the solvent in vacuo. Crystallize the residue from ethyl acetate to provide the title compound.

NMR (DMSO):δ=1.80–2.05(m,4), 2.34(s,3), 2.97(s,3), 3.75(m,1), 3.96(m,2), 6.09(s,1), 7.14(d,2), 7.19(d,2), and 9.68(s,1)ppm.

Example XXII 2,3-Dimethyl-8-[4-((methylsulfonyl)amino)phenyl]-5,6,7,8tetrahydroimidazo[1,5-a]pyridinium iodide In a manner known in the art employing the product of Example XXI and methyl iodide, there is obtained the subject compound.

NMR (DMSO):$\delta$=1.80–2.10(m,4), 2.56(s,3), 3.00(s,3), 3.69(s,3), 3.99–4.30(m,3), 7.04(s,1), 7.20(d,2), 7.25(d,2), and 9.76(s,1)ppm.

Example XXIII 5,6-Dihydro-2,3-dimethyl-8-[4-((methylsulfonyl)amino)-phenyl] imidazo[1,5-a]pyridinium iodide In a manner known in the art employing the product of Example VI and methyl iodide, there is obtained the subject compound.

NMR (DMSO):$\delta$=2.64(s,3), 2.72(quar,2), 3.04(s,3), 3,75(s,3), 4.20(t,2), 6.30(t,1), 7.28(d,2), 7.45(d,2), 7.61(s,1), and 9.95(s,1)ppm.

I claim:

1. A compound of the Formula 1

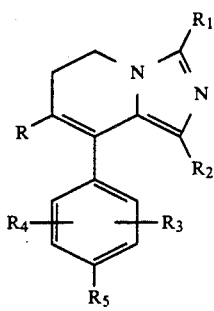

wherein R is hydrogen or lower alkyl;
$R_1$ is hydrogen, lower alkyl, halogen, amino, hydroxy or trifluoromethyl;
$R_2$ is hydrogen, halogen, lower alkyl, lower alkoxycarbonyl, aminocarbonyl, lower alkylaminocarbonyl or di-lower alkylaminocarbonyl;
$R_3$ and $R_4$ are the same or independently hydrogen, halogen, hydroxy, amino, nitro, aminocarbonyl, lower alkyl, lower alkoxy, lower alkanoylamino or lower alkylsulfonylamino;
$R_5$ is hydrogen, halogen, hydroxy, amino, lower alkyl, lower alkoxy, carboxy, lower alkanoylamino, lower alkysulfonylamino or 1-imidazolyl optionally substituted by 1 or more lower alkyl groups;
and the pharmaceutically acceptable acid addition, base addition and quaternary salts thereof.

2. A compound of claim 1 wherein $R_3$ and $R_4$ are hydrogen and $R_5$ is hydroxy, lower alkylsulfonylamino or 1-imidazolyl optionally substituted by 1 or more lower alkyl groups.

3. A compound of claim 1 which is 8-(4-chlorophenyl)-5,6-dihydro-3-methylimidazo[1,5-a] pyridine.

4. A compound of claim 1 which is 5,6-dihydro-8-(4-ethoxyphenyl)-3-methylimidazo[1,5-a] pyridine.

5. A compound of claim 1 which is 8-[4-(acetylamino)-phenyl] -5,6-dihydro-3-methylimidazo[1,5-a]pyridine.

6. A compound of claim 1 which is 5,6-dihydro-3-methyl-8-(4-methylphenyl)imidazo[1,5-a] pyridine.

7. A compound of claim 1 which is 8-(3,4-dichlorophenyl)-5,6-dihydro-3-methylimidazol[1,5-a] pyridine.

8. A compound of claim 1 which is 8-(4-chlorophenyl)-5,6-dihydro-3-ethyl-1-methylimidazo[1,5-a] pyridine.

9. A compound of claim 1 which is 5,6-dihydro-3-methyl-8-phenylimidazo[1,5-a] pyridine.

10. A compound of claim 2 which is 5,6-dihydro-8-(4-hydroxyphenyl)-3-methylimidazo[1,5-a] pyridine.

11. A compound of claim 2 which is 5,6-dihydro-3-methyl-8-[4-((methylsulfonyl)amino)phenyl] imidazo[1,5-a]-pyridine.

12. A compound of claim 2 which is 5,6-dihydro-2,3-dimethyl-8-[4-((methylsulfonyl)amino)phenyl] imidazo[1,5-a] pyridinium iodide.

13. A compound of claim 2 which is 5,6-dihydro-3-methyl-[4-(2-methyl-1H-imidazol-l-yl)phenyl] imidazo[1,5-a]-pyridine.

14. A compound of claim 2 which is 5,6-dihydro-3-ethyl-8-[(4-(2-ethyl-1H-imidazol-l-yl)phenyl] imidazo[1,5-a]pyridine.

15. A compound of claim 2 which is 5,6-dihydro-8-[4-(1H-imidazol-1-yl)phenyl] -3-methylimidazo[1,5-a]pyridine.

16. A pharmaceutical composition comprising at least one compound according to claim 1, together with one or more non-toxic pharmaceutically acceptable carriers.

* * * * *

UNITED STATES PATENT AND TRADEMARK OFFICE
CERTIFICATE OF CORRECTION

PATENT NO. : 5,026,712
DATED : June 25, 1991
INVENTOR(S) : David D. Davey It is certified that error appears in the above-identified patent and that said Letters Patent is hereby corrected as shown below:

Column 2, line 15

"The ouaternary salts contemplated" should read

.....The quaternary salts contemplated...

Column 2, line 46

"8-(4-methylphenvl)" should read

.....8-(4-methylphenyl).....

Column 4, line 8

"reacted t produce still other compounds" should read

.....reacted to produce still other compounds.....

Column 8, line 64

"hypotensive and CN stimulant effects." should read

.....hypotensive and CNS stimulant effects.....

Column 9, line 16

"(1H-imidazol-1yl" should read
--(1H-imidazol-1-yl--

UNITED STATES PATENT AND TRADEMARK OFFICE
CERTIFICATE OF CORRECTION

PATENT NO. : 5,026,712

DATED : June 25, 1991

INVENTOR(S) : David D. Davey

It is certified that error appears in the above-identified patent and that said Letters Patent is hereby corrected as shown below:

Column 9, line 36

"8-(4methylphenyl)" should read

.....8-(4-methylphenyl).....

Column 10, line 13

"NMR (CDCl$_3$): δ 175(s,2)," should read

.....NMR (CDCl$_3$): δ 1.75(s,1),.....

Column 10, line 14

"7.20-7.30(m,5," should read

.....7.20-7.30(m,5),.....

Column 11, line 25

"6,84(s,1)," should read

--6.84(s,1),--

UNITED STATES PATENT AND TRADEMARK OFFICE
CERTIFICATE OF CORRECTION

PATENT NO. : 5,026,712

DATED : June 25, 1991

INVENTOR(S) : David D. Davey

It is certified that error appears in the above-identified patent and that said Letters Patent is hereby corrected as shown below:

Column 11, line 33

"2methylimidazole and heat to 175°C." should read

..... 2-methylimidazole and heat to 175°C. ....

Column 11, line 37

"and 10.01(s1)ppm." should read

.... and 10.01(s,1)ppm. .....

Column 11, line 62

"7.10(d,2), 7.70(d,2)" should read

..... 7.10(d,2), 7.30(s,1), 7.70(d,2) ....

Column 12, line 63

"2methylimidazole and heat" should read

..... 2-methylimidazole and heat .....

UNITED STATES PATENT AND TRADEMARK OFFICE
CERTIFICATE OF CORRECTION

PATENT NO. : 5,026,712
DATED : June 25, 1991
INVENTOR(S) : David D. Davey It is certified that error appears in the above-identified patent and that said Letters Patent is hereby corrected as shown below:

Column 13, line 5

"cyclopropyl-3,4dichlorophenyl)" should read

--cyclopropyl-(3,4-dichlorophenyl)--.

Column 13, line 12

"6.82(S,1)," should read

..... 6.82(s,1), .....

Column 13, line 29

"vacuum to 200 ml rotal" should read

..... vacuum to 200 ml total .....

Column 14, line 27

"extract with 2-1.5 liters" should read

..... extract with 2 x 1.5 liters .....

UNITED STATES PATENT AND TRADEMARK OFFICE
CERTIFICATE OF CORRECTION

PATENT NO. : 5,026,712

DATED : June 25, 1991

INVENTOR(S) : David D. Davey

It is certified that error appears in the above-identified patent and that said Letters Patent is hereby corrected as shown below:

Column 15, line 4

"-5,6,7,8tetrahydroimidazo" should read

..... -5,6,7,8-tetrahydroimidazo .....

Column 16, line 36

"-3-methyl-[4-(2-methyl-" should read

..... -3-methyl-8-[4-(2-methyl- .....

Signed and Sealed this

Twenty-first Day of June, 1994

*Attest:*

BRUCE LEHMAN

*Attesting Officer*     *Commissioner of Patents and Trademarks*